(12) United States Patent
Wimpenny et al.

(10) Patent No.: US 7,090,662 B2
(45) Date of Patent: Aug. 15, 2006

(54) DOSE DIAL AND DRIVE MECHANISMS SUITABLE FOR USE IN DRUG DELIVERY DEVICES

(75) Inventors: Steven Wimpenny, Leamington Spa (GB); David Aubrey Plumptre, Droitwich (GB); Robert Frederick Veasey, Leamington Spa (GB)

(73) Assignee: DCA Design International Ltd., Warwick (GB)

( * ) Notice: Subject to any disclaimer, the term of this patent is extended or adjusted under 35 U.S.C. 154(b) by 74 days.

(21) Appl. No.: 10/805,246

(22) Filed: Mar. 22, 2004

(65) Prior Publication Data

US 2004/0249348 A1 Dec. 9, 2004

(30) Foreign Application Priority Data

Mar. 22, 2003 (GB) .................... 0306642

(51) Int. Cl.
*A61M 5/315* (2006.01)
(52) U.S. Cl. .............. 604/207; 604/604; 604/208
(58) Field of Classification Search ............... 604/207, 604/208, 218, 232
See application file for complete search history.

(56) References Cited

U.S. PATENT DOCUMENTS

| 5,017,190 | A | * | 5/1991 | Simon et al. ............. 604/207 |
| 5,304,152 | A | | 4/1994 | Sams |
| 5,626,566 | A | * | 5/1997 | Petersen et al. ........... 604/208 |
| 5,674,204 | A | | 10/1997 | Chanoch |
| 5,688,251 | A | | 11/1997 | Chanoch |
| 5,984,900 | A | * | 11/1999 | Mikkelsen ................ 604/208 |
| 6,004,297 | A | * | 12/1999 | Steenfeldt-Jensen et al. .... 604/207 |
| 6,106,501 | A | | 8/2000 | Michel |
| 6,364,860 | B1 | | 4/2002 | Steck et al. |
| 2002/0120235 | A1 | * | 8/2002 | Enggaard ................. 604/135 |
| 2004/0059299 | A1 | | 3/2004 | Moller et al. |

FOREIGN PATENT DOCUMENTS

| DE | 3814023 A1 | 1/1989 |
| EP | 0 295 075 B1 | 12/1988 |
| EP | 0554996 B1 | 8/1993 |
| EP | 0 615 762 B1 | 9/1994 |
| EP | 0 937 471 A2 | 8/1999 |
| EP | 937471 A2 * | 8/1999 |
| WO | WO 91/14467 | 10/1991 |
| WO | WO 96/26754 A | 9/1996 |
| WO | WO 99/38554 | 8/1999 |

* cited by examiner

*Primary Examiner*—Manuel A Mendez
*Assistant Examiner*—Melissa A. McCorkle
(74) *Attorney, Agent, or Firm*—Finnegan, Henderson, Farabow, Garrett & Dunner

(57) ABSTRACT

A dose dial and drive mechanism for use in a drug delivery device having a housing, a dose dial sleeve, a piston rod, a drive sleeve threadedly connected to the piston rod, a reset sleeve, which is located between the drive sleeve and the housing, and a dose display. When the dose dial sleeve travels towards the second end of the housing the reset sleeve is carried with the dose dial sleeve towards the second end of the housing resetting the dose display to a zero position and when the dose dial sleeve and/or the reset sleeve travels towards the first end of the housing, the dose dial sleeve and/or reset sleeve engage(s) with the drive sleeve thus advancing both the drive sleeve and the piston rod towards the first end of the housing.

12 Claims, 3 Drawing Sheets

DOSE DIAL AND DRIVE MECHANISMS SUITABLE FOR USE IN DRUG DELIVERY DEVICES

THE TECHNICAL FIELD OF THE INVENTION

The present invention relates to dose dial and drive mechanisms suitable for use in drug delivery devices, in particular pen-type injectors, having dosage setting means, enabling the administration of medicinal products from a multidose cartridge. In particular, the present invention relates to such drug delivery devices where a user may set the dose.

DESCRIPTION OF RELATED ART

Such drug delivery devices have application where regular injection by persons without formal medical training occurs, i.e., patients. This is increasingly common amongst those having diabetes where self-treatment enables such persons to conduct effective management of their diabetes.

These circumstances set a number of requirements for drug delivery devices of this kind. The device must be robust in construction, yet easy to use in terms of the manipulation of the parts, understanding by a user of its operation and the delivery of the required dose of medicament. Dose setting must be easy and unambiguous. In the case of those with diabetes, many users will be physically infirm and may also have impaired vision requiring the drive mechanism to have low dispensing force and an easy to read dose setting display. Where the device is to be disposable rather than reusable, the device should be cheap to manufacture and easy to dispose of (preferably being suitable for recycling). To meet these requirements the number of parts required to assemble the device and the number of material types the device is made from need to be kept to a minimum.

User operated drug delivery devices comprising dose dial and drive mechanisms are well known within the medical field.

DE3814023 A1 discloses an injection device based on the ball point pen principle. The device has a cartridge containing a drug, in particular insulin, from which two insulin units can be injected by depressing a button. The movement of the button causes a longitudinally movable tubular piston rod to engage with and move a longitudinally displaceable syringe piston located in the cartridge. The device of DE 3814023 A1 does not address me problem of incorrect dose setting by the user.

EP0554996 A1 discloses an injection device, comprising a drive mechanism and a dose setting means comprising a unit counter ring and a tens counter ring. The tens counter ring Is positioned in adjoining relation to the units counter ring, with both rings being connected by a transmission means. The transmission means includes means for causing the tens counter ring to rotate a selected number of degrees upon rotation of the unit counter ring through a selected angular displacement. The device also includes means that react to the dose setting means for controlling the axial movement of the piston rod. The device enables the user to select a dosage and allows the rectification of overdose situations without dispensing the medicament. However, reset of the dose setting means to a zero position requires the user to rotate the dose setting means back to the zero position thus requiring additional user operations.

Surprisingly it was found that the dose dial and drive mechanism according to instant invention provides the user with an automatic reset for the dose dial mechanism, which allows easy resetting of the dose display without requiring additional user operations. This automatic reset to a zero position contributes to safe dose dialing and dispensing.

DESCRIPTION OF THE INVENTION

According to a first aspect of the present invention, a dose dial and drive mechanism for use in a drug delivery device is provided, comprising a housing;

a dose dial sleeve;

a piston rod;

a drive sleeve is threadedly connected to the said piston rod;

a reset sleeve, which is located between said drive sleeve and said housing; and a dose display, characterised in that
   a) when said dose dial sleeve travels towards the second end of said housing the reset sleeve is carried with said dose dial sleeve towards the second end of said housing thereby resetting said dose display to a zero position; and
   b) when said dose dial sleeve and/or the reset sleeve travels towards the first end of said housing, the said dose dial sleeve and/or reset sleeve engage(s) with said drive sleeve thus advancing both said drive sleeve and said piston rod towards the first end of said housing.

The term "drug delivery device" according to instant invention shall mean a single-dose or multi-dose, disposable or re-useable device designed to dispense a selected dose of a medicinal product, preferably multiple selected dose, e.g. insulin, growth hormones, low molecular weight heparins, and their analogues and/or derives etc. Said device may be of any shape, e.g. compact or pen-type. Dose delivery may be provided through a mechanical (optionally manual) or electrical drive mechanism or stored energy drive mechanism, such as a spring, etc. Dose selection may be provided through a manual mechanism or electronic mechanism. Additionally, said device may contain components designed to monitor physiological properties such as blood glucose levels, etc. Furthermore, the said device may comprise a needle or may be needle-free. In particular, the term "drug delivery device" shall mean a disposable multi-dose pen-type device having mechanical and manual dose delivery and dose selection mechanisms, which is designed for regular use by persons without formal medical training such as patients. Preferably, the drug delivery device is of the injector-type.

The term "housing" according to instant invention shall preferably mean any exterior housing ("main housing", "body", "shell") or interior housing ("insert", "inner body"). The housing may be designed to enable the safe, correct, and comfortable handling of the drug delivery device or any of its mechanism. Usually, it is designed to house, fix, protect, guide, and/or engage with any of the inner components of the drug delivery device (e.g., the drive mechanism, cartridge, plunger, piston rod) by limiting the exposure to contaminants, such as liquid, dust, dirt etc. In general, the housing may be unitary or a multipart component of tubular or non-tubular shape. Usually, the exterior housing serves to house a cartridge from which a number of doses of a medicinal product may by dispensed.

The term "engaged" according to instant invention shall particularly mean the interlocking or abutment of two or more components of the 'dose dial and drive mechanism'/ drug delivery device, e.g. a spline or thread connection, preferably the interlocking of helical threads of components ("threadedly engaged").

The term "helical thread" according to instant invention shall preferably mean a full or part thread, e.g., a cylindrical spiral rib/groove, located on the internal and/or external surface of a component of the drug delivery device, having an essentially triangular or square or rounded section designed to allow continuous free rotational and/or axial movement between components. Optionally, said thread may be further designed to prevent rotational or axial movement of certain components in one direction.

The "dose dial sleeve" according to instant invention shall allow the user to select the amount of drug to be dispensed. It shall mean an essentially tubular component of essentially circular cross-section, optionally disposed for axial movement in me housing, which preferably comprises a first cylinder of a first diameter and a second cylinder of a second diameter concentrically disposed with respect to one another, whereby the value of the said first diameter is lower than the value of the said second diameter. Preferably, the "dose dial sleeve" extends from the second end of the housing and engages both with the dose display, preferably the first cylindrical wheel, and the reset sleeve.

The dose dial sleeve according to instant invention is designed to travel between the first and the second end of the housing, e.g., driven by the users actuation force and/or by the stored energy of a spring means, an electrical motor, etc.

The term "dose display" according to instant invention shall mean a means for displaying the dosage of the drug to be dispensed by the user. This may be achieved by the use of markings, symbols, numerals, etc., e.g. printed on the external surface of the dose dial sleeve or an odometer, or the like. In an alternative embodiment said dose display may be an electronic display means.

In a more specific embodiment of instant invention, the dose display comprises two adjacent cylindrical wheels located within the housing and being disposed for rotation with respect to the housing, wherein one cylindrical wheel displays unit dosage measures and the other cylindrical wheel tens dosage measures.

The term "preset sleeve" according to instant invention shall mean any essentially tubular component of essentially circular cross-section located between the drive sleeve and the housing and engages with the first and second cylindrical wheels of said dose display, optionally by means of a gear component. The reset sleeve is designed to reset the said first and second cylindrical wheels of the dose display to a zero position when it is moved towards the second end of the housing. Preferably, the reset sleeve engages with the inner surface of said first and second cylindrical wheels by means of teeth.

The term "drive sleeve" according to instant invention shall mean any essentially tubular component of essentially circular cross-section, which is engaged with the piston rod, preferably threadedly engaged.

In a more particular embodiment of instant invention, the drive sleeve is disposed within the first cylinder of the dose dial sleeve.

The term "piston rod" according to instant invention shall mean any component adapted to operate through/within the housing, designed to translate axial movement through/ within the drug delivery device, preferably from the drive sleeve to the piston, for the purpose of discharging/dispensing an injectable product. Said piston rod may be flexible or not. It may comprise a simple rod, a lead-screw, a rack and pinion system, a worm gear system, or the like. The piston rod of instant invention shall further mean a component having a circular or non-circular cross-section. It may be made of any suitable material known by a person skilled in the art.

The term "zero position" according to instant invention shall mean when both said cylindrical wheels of said dose display indicate the number zero.

The term "first end" according to instant invention shall mean the proximal end. The proximal end of the device or a component of the device shall mean the end, which is closest to the dispensing end of the device.

The term "second end" according to instant invention shall mean the distal end.

The distal end of the device or a component of the device shall mean the end, which is furthest away from the dispensing end of the device.

A second aspect of instant invention provides an assembly for use in a drug delivery device comprising the dose dial and drive mechanism according to instant invention.

A third aspect of the present invention provides a drug delivery device comprising the dose dial and drive mechanism or the assembly according to instant invention.

A fourth aspect of the present invention provides a method of assembling a drug delivery device comprising the step of providing a dose dial and drive mechanism or an assembly according to instant invention.

A fifth aspect of instant invention is the use of a drug delivery device according to instant invention for dispensing a medicinal product preferably dispensing a pharmaceutical formulation (e.g. solution, suspension etc.) comprising an active compound selected from the group consisting of insulin, growth hormone, low molecular weight heparin, their analogues and their derivatives.

BRIEF DESCRIPTION OF THE DRAWINGS

Without any limitation, the instant invention will be explained in greater detail below in connection with a preferred embodiment and with reference to the drawings in which.

Figure 1:
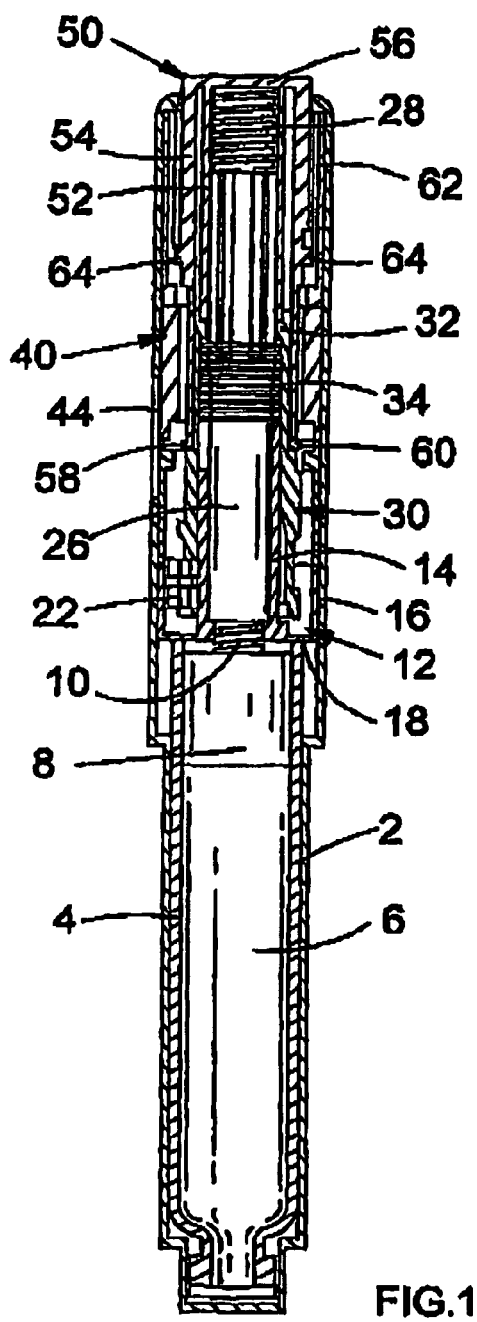
FIG. 1 shows a sectional side view of an injector in accordance with the present invention in a first position.

Referring first to FIG. 1 there is seen an injector in accordance with the present invention. The injector comprises a housing 2 within which are located a cartridge 4 containing a medicinal product, means for selecting or setting of the dose of medicinal product to be expelled and means for expelling the selected dose of medicinal product. The housing 2 is generally cylindrical in shape and is divided into two compartments.

The cartridge 4 is located within a first compartment of the housing 2 while the dose setting means and the means for expelling the selected dose of medicinal product are located within a second compartment of the housing 2. The medicinal product may be expelled from the cartridge 4 by advancing a piston 8 towards a first end of the injector, in use, a needle unit (not shown) is attached to the first end of the housing 2 through which the medicinal product may flow.

The piston 8 may be advanced under the action of a threaded piston rod 10. An insert 12 is located in the housing 2. The insert 12 comprises an inner portion 14 and an outer portion 16 connected by a central web 18. The inner portion 14 includes an opening 20 through which the piston rod 10 may pass. The opening 20 is surrounded by a generally cylindrical portion extending from the insert towards a second end of the injector. The generally cylindrical portion includes spline (not shown) against which a gear component 22 is located. The outer portion 16 of the insert 12 comprises a generally cylindrical part. The outer portion 16 of the insert 12 is secured in the housing 2 by any suitable means, e.g., a clip, an adhesive etc. A channel is formed between the generally cylindrical part of the inner portion 14 of the insert 12 and the generally cylindrical part of the outer portion 16 of the insert 12.

A first sleeve in the form of a drive sleeve 26 of generally cylindrical configuration surrounding the piston rod 10 is located between the piston rod 10 and the generally cylindrical portion 14. A second end of the drive sleeve 26 is provided with a moulded spring 28. The drive sleeve 26 has an internal thread (not shown) for threaded engagement with the threaded piston rod 10.

A reset sleeve 30 is located about the generally cylindrical portion of the inner portion of the insert 12 and so also about the drive sleeve 26. In the region of the generally cylindrical portion 14 of the insert 12 the reset sleeve 30 is conveniently splined to the generally cylindrical portion 14 of the insert 12. Beyond the generally cylindrical portion of the insert 12 the reset sleeve 30 includes a radially inwardly directed lug or flange 32. A compression spring 34 is disposed about the drive sleeve 26 between a second end of the generally cylindrical portion 14 of the insert 12 and a first face of the inwardly directed flange 32 of the reset sleeve 30. The gear component 22 is carried from a first end of the reset sleeve 30. The gear component 22 is conveniently carried by a snap in moulded bearing such that the gear component 22 is able to rotate about an axis defined by the bearing. The reset sleeve 30 further includes a shoulder 36 disposed between the first and second ends of the reset sleeve 30.

A first cylindrical wheel 42 is located within the housing 2 adjacent the outer portion 16 of the insert 12. The first cylindrical wheel 42 is adapted to rotate within the housing 2. A second cylindrical wheel 40 is located within the housing 2 adjacent the first cylindrical wheel 42. The second cylindrical wheel 40 is also adapted for rotation within the housing 2. Each of the first and second cylindrical wheels 42,40 is provided with means releasably to engage the gear component 22. In this way, the gear component 22 is adapted to control the relative movement of the first and second cylindrical wheels 42,40. Each of the first and second cylindrical wheels 42,40 is provided with numerals about an outer circumference. The reference numerals may be viewed through a window 44 in the housing 2. The second cylindrical wheel 40 may be used to represent single units of ° dosage of a medicinal product and the first cylindrical wheel 42 may be used to represent ten units of dosage. In this instance the gear component 22 is used to advance the first cylindrical wheel 42 one increment every tenth increment of the second cylindrical wheel 40.

A dose dial sleeve 50 is provided comprising a first cylinder 52 and a second cylinder 54 substantially concentrically disposed about the first cylinder 52. An end web 56 extends across a second end of the first cylinder 52 and a second end of the second cylinder 54. The second end of the drive sleeve 26 including the moulded spring 28 is disposed within in the first cylinder 52 of the dose dial sleeve 50. A second end of the dose dial sleeve 50 extends through an opening in the second end of the housing 2.

A first end of the first cylinder 52 is adapted to be seated against a second face of the inwardly directed flange 32 of the reset sleeve 30.

The second cylinder 54 extends axially beyond the first cylinder 52. A first end of the second cylinder 54 is adapted to abut the shoulder 36 of the reset sleeve 30. The first end of the second cylinder 54 is further provided with means to engage with the first cylindrical wheel 42. In the illustrated embodiment, the first end of the second cylinder 54 is provided with two radially extending lugs 58,60 which drive axially disposed radially inwardly extending lugs (not shown) formed on the inside of the first cylindrical wheel 42.

A third sleeve 62 is located in the housing 2 axially between the second cylindrical wheel 40 and the second end of the housing 2. The third sleeve 62 comprising a series of internal channels (not shown), the channels comprising an interconnected alternating series of open and closed channels. The second cylinder 54 of the dose dial sleeve 50 further includes at least one radially outwardly extending lug 64 for engaging in the channels.

In the initial position of FIG. 1 the at least one radially outwardly extending lug 64 engages one of the closed channels in the third sleeve 62.

Figure 2:
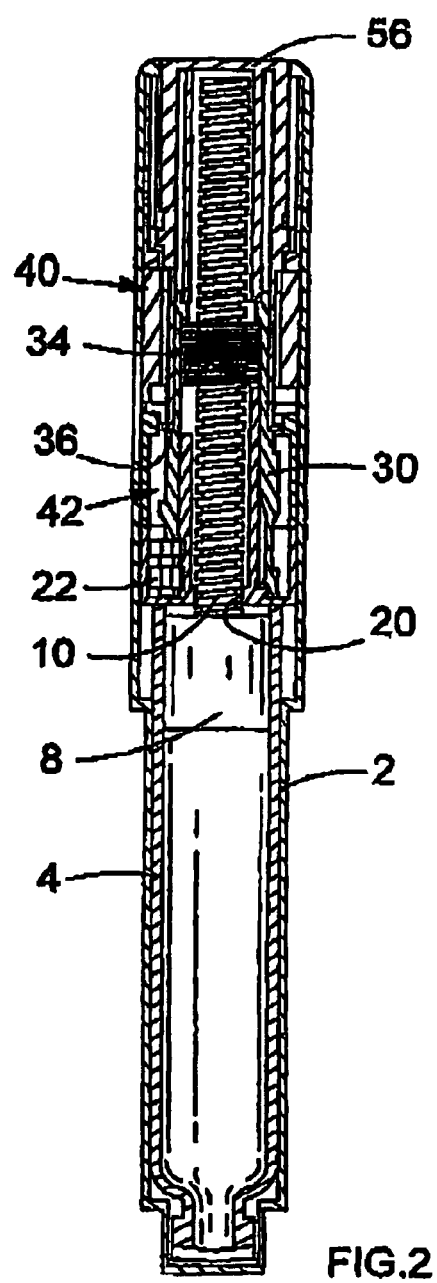
FIG. 2 shows a sectional side view of the injector of FIG. 1 (with a drive sleeve omitted for clarity) in a second position.

To release the dose dial sleeve 50 a user presses on the end of the dose dial sleeve 50 (as shown in FIG. 2). This causes the at least one radially outwardly extending lug 64 to move within the internal channels of the third sleeve 62 towards the first end of the housing 2. The dose dial sleeve 50 is guided by the channels slightly in rotation as the dose dial sleeve 50 moves toward the first end of the housing. The slight rotation aligns the at least one radially outwardly extending lug 64 with one of the open channels in the third sleeve 62. Then under the action of the compression spring 34 the dose dial sleeve 50 pops out beyond the second end of the housing 2.

As the dose dial sleeve 50 travels out (under the action of the compression spring 34), the dose dial sleeve 50 carries the reset sleeve 30 with it. The reset sleeve 30 has teeth that engage with features on the inside of the first and second cylindrical wheels 42,40. This movement of the reset sleeve 30 causes the teeth of the reset sleeve 30 to reset to zero the first and second cylindrical wheels 42,40 of the dose display.

Figure 3:
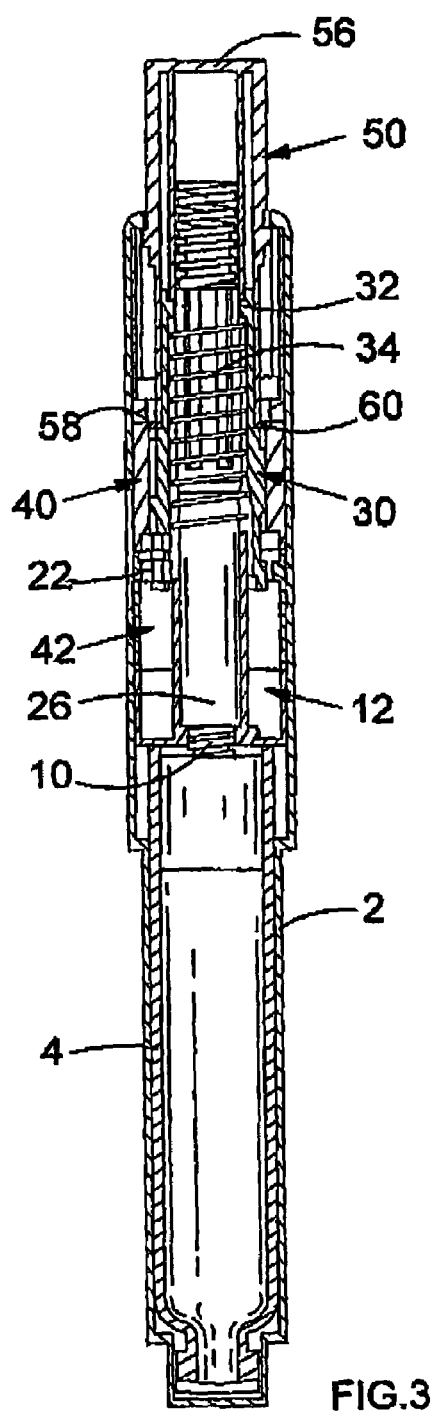
FIG. 3 shows a sectional side view of the injector of FIG. 1 in a third position.

In this third position (FIG. 3), the gear component 22 is disposed in a cut away region of the generally cylindrical portion of the insert 12 and is free to rotate.

Figure 4:
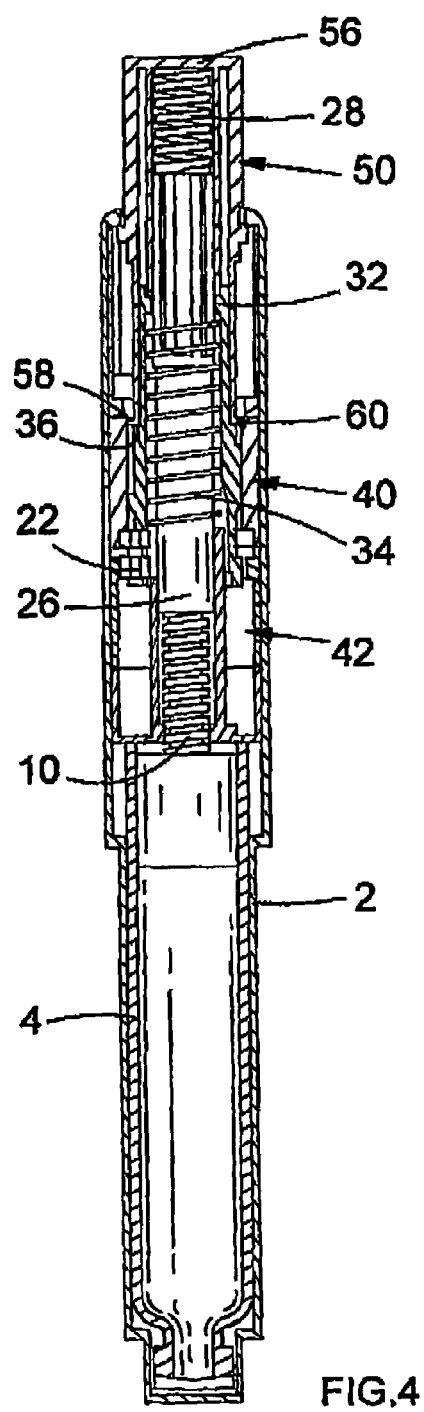
FIG. 4 shows a sectional side view of the injector of FIG. 1 in a fourth position.

The user may then rotate the dose dial sleeve 50 which in turn causes the drive sleeve 26, which is threaded to the piston rod 10 to be advanced towards the second end of the housing 2 and the end web 56 of the dose dial sleeve 50 (FIG. 4). Rotation of the dose dial sleeve 50 causes the two radially extending lugs 58,60 to drive the second cylindrical wheel 40. Sufficient rotation of the dose dial sleeve 50 will cause the first cylindrical wheel 42 to be driven through the gear component 22 by the second cylindrical wheel 40.

Figure 5:
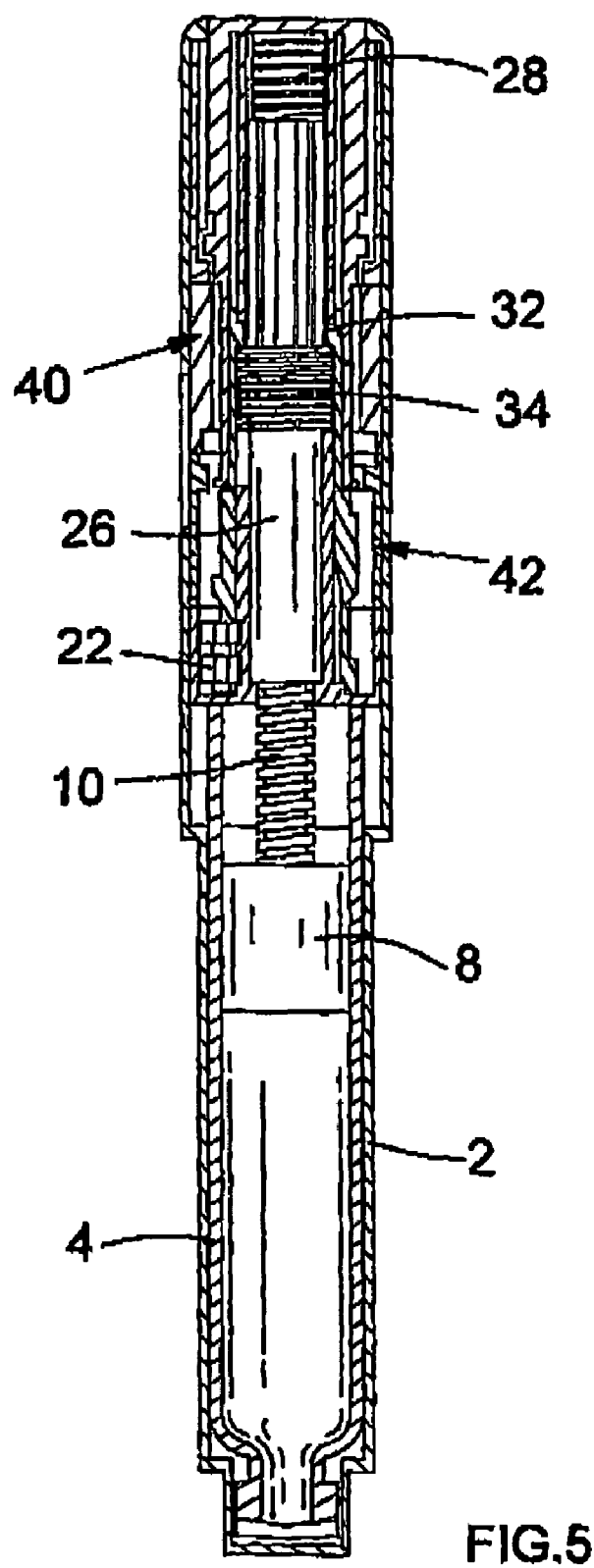
FIG. 5 shows a sectional side view of the injector of FIG. 1 in a fifth position.

To dispense a dose the user presses on the web 56 of the dose dial sleeve 50. The dose dial sleeve 50 then drives the reset sleeve 30 axially. The dose dial sleeve 50 engages with the drive sleeve 26 and advances both the drive sleeve 26 and the piston rod 10 against the cartridge piston 8. The dose that was selected remains displayed by the first and second cylindrical wheels 42,40. In the home position (shown in FIG. 5) the dose dial sleeve 50 locks the first and second cylindrical wheels 42,40 to prevent the first and second cylindrical wheels 42,40 from rotating when the injector is not in use.

The moulded spring 28 at the dial end of the drive sleeve 26 ensures that the piston rod 10 does not retract from a second face of the cartridge piston 8 after the dose dial sleeve 50 has been released.

The invention claimed is:

1. A dose dial and drive mechanism for use in a drug delivery device comprising:
   a housing having a first end closest to a dispensing end of the device and a second end opposite the first end;
   a dose dial sleeve;
   a piston rod;
   a drive sleeve is threadedly connected to the said piston rod;
   a reset sleeve, which is located between said drive sleeve and said housing; and
   a dose display,
   characterized in that
   a) when said dose dial sleeve travels towards the second end of said housing the reset sleeve is carried with said dose dial sleeve towards the second end of said housing thereby resetting said dose display to a zero position; and
   b) when said dose dial sleeve and/or the reset sleeve travels towards the first end of said housing, the said dose dial sleeve and/or reset sleeve engage(s) with said drive sleeve thus advancing both said drive sleeve and said piston rod towards the first end of said housing.

2. A method of assembling a drug delivery device comprising:
   providing a dose dial and drive mechanism including:
     a housing having a first end closest to a dispensing end of the device and
     a second end opposite the first end;
     a dose dial sleeve;
     a piston rod;
     a drive sleeve threadedly connected to the piston rod;
     a reset sleeve located between the drive sleeve and the housing; and
     a dose display; and
   arranging the dose dial and the drive mechanism such that:
     (a) when the dose dial sleeve travels towards the second end of the housing, the reset sleeve is carried with the dose dial sleeve towards the second end of the housing, thereby resetting the dose display to a zero position; and
     (b) when the dose dial sleeve and/or the reset sleeve travels towards the first end of the housing, the dose dial sleeve and/or the reset sleeve engages with the drive sleeve thus advancing both the drive sleeve and the piston rod towards the first end of the housing.

3. A method of delivering a drug comprising:
   providing a dose dial and drive mechanism including
     a housing having a first end closest to a dispensing end of the device and
     a second end opposite the first end;
     a dose dial sleeve;
     a piston rod;
     a drive sleeve threadedly connected to the piston rod;
     a reset sleeve located between the drive sleeve and the housing; and
     a dose display; and
   wherein the dose dial and the drive mechanism are configured such that
     (a) when the dose dial sleeve travels towards the second end of the housing, the reset sleeve is carried with the dose dial sleeve towards the second end of the housing, thereby resetting the dose display to a zero position; and
     (b) when the dose dial sleeve and/or the reset sleeve travels towards the first end of the housing, the said dose dial sleeve and/or the reset sleeve engages with the drive sleeve thus advancing both the drive sleeve and the piston rod towards the first end of the housing;
   and
   dispensing a drug comprising an active compound selected from the group consisting of insulin, growth hormone, low molecular weight heparin, their analogues and their derivatives.

4. The mechanism of claim 1, further comprising a compression spring within the housing configured to move the reset sleeve and the dose dial sleeve towards the second end of the housing after the dose dial sleeve is moved a predetermined distance toward the first end of the housing.

5. The mechanism of claim 1, further comprising at least one cylindrical wheel within the housing, the at least one cylindrical wheel including indicia designating a particular dosage on an outer circumference thereof.

6. The mechanism of claim 5, wherein the dose dial sleeve includes engagement features configured to engage and drive corresponding engagement features on an inside surface of the at least one cylindrical wheel.

7. The mechanism of claim 5, wherein the reset sleeve includes engagement features configured to engage and reset to zero the at least one cylindrical wheel upon movement of the reset sleeve towards a second end of the housing.

8. The mechanism of claim 5, wherein the mechanism is configured such that when the dose dial sleeve travels to a furthest point towards the first end of the housing, a locking mechanism prevents movement of the at least one cylindrical wheel.

9. The mechanism of claim 1, wherein the housing includes a first cylindrical wheel including indicia designating increments of 10 dosage units and a second cylindrical wheel including indicia designating single dosage units.

10. The mechanism of claim 9, wherein the reset sleeve includes a gear component configured to advance the first cylindrical wheel one increment for every tenth increment of the second cylindrical wheel.

11. The method of claim 3, wherein dispensing a drug includes selecting a dose level by:
   moving the dose dial sleeve a predetermined distance toward the first end of the housing; and
   rotating the dose dial sleeve a predetermined amount corresponding to a particular dosage.

12. The method of claim 11, wherein the dose dial and the drive mechanism include at least one cylindrical wheel within the housing, the at least one cylindrical wheel including indicia designating a particular dosage on an outer circumference thereof and wherein rotating the dose dial sleeve causes a change in the indicia viewable through the dose display.

* * * * *